US007524627B2

(12) United States Patent
Corvaia et al.

(10) Patent No.: US 7,524,627 B2
(45) Date of Patent: Apr. 28, 2009

(54) METHOD OF GENERATING AND/OR INCREASING AN IMMUNE RESPONSE AGAINST RSV

(75) Inventors: Nathalie Corvaia, St. Julien En Genevois (FR); Thien Ngoc Nguyen, St. Julien En Genevois (FR); Alain Beck, Collonges Sous Saleve (FR); Hélène Plotnicky, Allonzier la Caille (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 0 days.

(21) Appl. No.: 11/985,839

(22) Filed: Nov. 16, 2007

(65) Prior Publication Data

US 2009/0036367 A1    Feb. 5, 2009

Related U.S. Application Data

(62) Division of application No. 10/484,298, filed as application No. PCT/FR02/02599 on Jul. 19, 2002, now Pat. No. 7,309,494.

(30) Foreign Application Priority Data

Jul. 20, 2001    (FR) .................................. 01/09731

(51) Int. Cl.
*C12Q 1/70* (2006.01)
*A61K 39/12* (2006.01)
(52) U.S. Cl. ...................... 435/5; 424/186.1; 424/211.1
(58) Field of Classification Search ........................ None
See application file for complete search history.

(56) References Cited

U.S. PATENT DOCUMENTS 5,223,254 A    6/1993    Paradiso et al.

FOREIGN PATENT DOCUMENTS

| WO | WO 8704185 | 7/1987 |
|---|---|---|
| WO | WO 9527787 | 10/1995 |
| WO | WO 9746581 | 12/1997 |
| WO | WO 9903987 | 1/1999 |
| WO | WO 9949892 | 10/1999 |
| WO | WO 0121203 | 3/2001 |

OTHER PUBLICATIONS

Varga, et al., Journal of Immunology, 2000, 165:6487-6495.
Olins, et al., Current Opinion in Biotechnology, 1993, 520-525.
Smith, et al. Comparison of Biosequences, Advances in Applied Mathematics, 1981, 2:482-489.
Needleman,et al., J. Mol. Biol. 1970, 48:443-453.
Pearson, et al., Improved tools for biological sequence comparison, Proc. Natl. Acad. Sci. USA, 1988, 85:2444-2448.
Trudel, et al., Identification of a synthetic peptide as part of a major neutralization epitope of respiratory syncytial virus, J. Gen. Virol., 1987, 68:2273-2280.
Trudel, et al., Respiratory Syncytial Virus fusion glycoprotein: further characterization of a major epitope involved in virus neutralization, Can. J. Microbiol. vol.33, 1987.
Vella, et al., Infection and Immunity, Dec. 1992, pp. 4977-4983.
Lopez, et al., Location of a highly conserved neutrlaizng eptiope in the F glycoprotein of human respiratory syncytial virus, Journal of Virology, Feb. 1990, pp. 927-930.
Haeuw, et al., Eur. J. Biochem., 1998, 255:446-454.
Johnson, et al., Proc. Natl. Acad. Sci. USA, 1987 84:5625-5629.
Sparer, et al., J. Exp. Med, 1998, 187:1921-1926.
King, et al., Expression, purification and characterization of B72.3 Fv fragments, Biochem. J., 1993,290:723-729.
Scopes, et al., Identification of a linear epitope on the fusion glycoprotein of respiratory syncytial virus, J. Gen. Virol., 1990, 71:53-59.
Fusco, et al., The Journal of Infectious Diseases, 1997, 175:364-372.
Croft, et al., The Journal of Immunology, 1991, 146:793-798.
Mountain,et al., Biotechnology and Genetic Engineering Reviews, 1992, 10:1-142.
Simard, et al., Vaccine, 1997, 15:423-432.
Von Hunolstein, et al., Vaccine, 2001, 19:3058-3066.
Hyun Vha Kim, et al., Pediat. Res., 1976, 10:75-78.
Plotnicky-Gilquin, et al., Journal of Virology, Jul. 1999, pp. 5637-5645.
Goeddel, David Gene expression technology, Methods in Enzymology, vol. 185, 1990.
Kohler, G. Continuous cultures of fused cells secreting antibody of predefined specificity, Nature, vol. 256, 1975.
Skerra, et al., Assembly of a functional immunoglobulin F fragment in *Escherichia coli*, Science, 1988, 240:1038-1041.
Geysen, et al., Strategies for eptiope analysis using peptide synthesis, Journal of Immunological Methods, 1987, 102:259-174.
Carter, et al., Proc. Natl. Acad. Sci. USA, 1992, 89:4285-4289.
Doreleijers, et al. Biochemistry, 1996, 35:14684-14688.

*Primary Examiner*—Stacy B Chen
(74) *Attorney, Agent, or Firm*—Hueschen and Sage

(57) ABSTRACT

The present invention relates to the Respiratory Syncytial Virus, and more particularly to the identification of novel antigens which are useful in particular for the therapeutic and prophylactic treatment of conditions caused by this virus. The present invention relates to methods of generating and/or increasing an immunogenic response directed against Respiratory Syncytial Virus, including subgroups A and B.

7 Claims, 3 Drawing Sheets

Figure 1A:
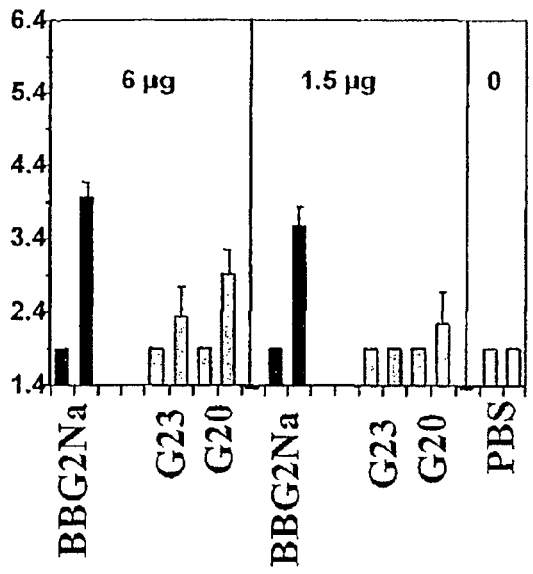

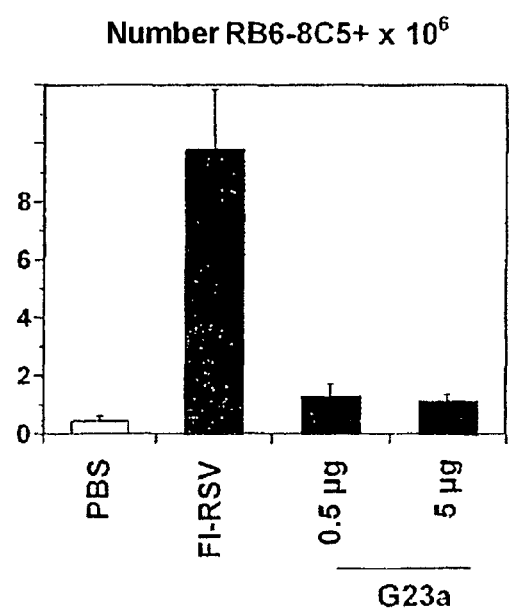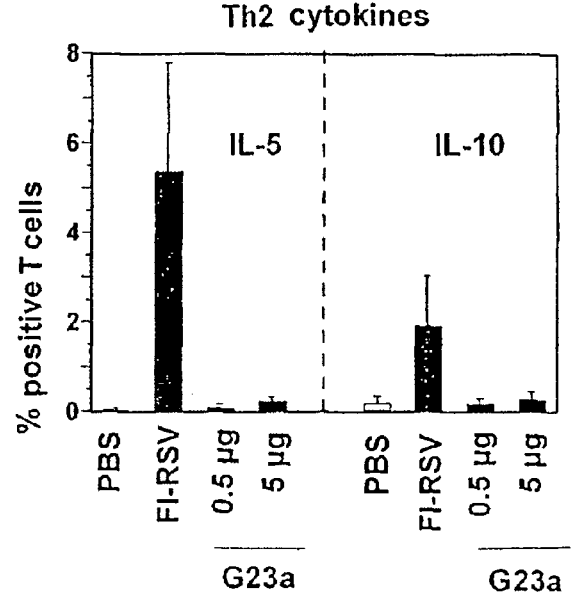
FIGURE 5A                                   FIGURE 5B

METHOD OF GENERATING AND/OR INCREASING AN IMMUNE RESPONSE AGAINST RSV

This application is a division of U.S. Ser. No. 10/484,298, filed Jan. 20, 2004, now U.S. Pat. No. 7,309,494, which is a national stage filing of PCT/FR02/02599, filed Jul. 19, 2002.

The present invention relates to the respiratory syncytial virus, and more particularly to the identification of novel antigens which are useful in particular for the therapeutic and prophylactic treatment of conditions caused by this virus.

The respiratory syncytial virus (RSV) is classified in the Paramyxoviridae family, genus pneumovirus, comprising a nonsegmented RNA genome of negative polarity encoding 11 specific proteins.

RSV is one of the etiological agents most commonly encountered in infants and in elderly individuals. Bronchiolitis is often serious in children and requires hospitalization. Currently, there are no means of prevention against the disease due to RSV. The first infection with RSV does not protect against the following one. Treatment of serious cases with antibiotics (ribavirin) and/or combined with immunotherapy (human immunoglobulins) cannot reduce the worsening of the disease. A humanized monoclonal antibody directed against the RSV F protein, called palivizumab (Synagis TM), has also been developed. However, this type of treatment still remains very expensive. During the 1960s, attempts to immunize children with a formalin-inactivated RSV vaccine (FI-RSV) had resulted in worsening of the disease instead of conferring protection against natural infection with RSV. This worsening of the disease was characterized by an increase in neutrophils, in lymphocytes and in eosinophils in the blood and lungs (Kim et al., Pediatric Res., 10:75-78, 1976). It was also demonstrated in mice that FI-RSV induced a Th2 type (T-helper 2) immune response, resulting in particular in a considerable production of IL-4, IL-5, IL-10 and IL-13, which are Th2 cytokines. Recent studies have made it possible to correlate this immunopathology observed subsequent to administration of FI-RSV with a precisely determined region, a CD4+ epitope of sequence 185-193 of the G protein (ICKRIPNKK, SEQ ID No. 10), which proves to be essential for obtaining a Th2 cytokine response in mice (Varga et al., J. Immunol., 165:6487-6495, 2000).

Application WO 87/04185 has proposed using RSV structural proteins with a view to a vaccine, such as the envelope proteins called F protein (fusion protein) or G protein (attachment protein), a 22 Kd glycoprotein, a 9.5 Kd protein, or the major capsid protein (N protein).

Application WO 89/02935 describes the protective properties of the whole F protein of RSV, optionally modified in monomeric or deglycosylated form.

In application WO 95/27787, it has been shown that the RSV G protein may be useful in the preparation of products intended for the treatment and/or for the prevention of conditions caused by RSV subgroup A or B.

Peptides which are structurally homologous to the sequence 149-197 of the G protein and in which no oligosaccharide is bound to a serine, threonine or asparagine are described in application WO 97/46581.

As regards application WO 99/03987, it describes fragments of the RSV G protein, containing specific epitopes, used in a vaccine against RSV infection.

However, none of these applications has solved the problem of the development of RSV antigens for obtaining both a sufficient and protective immune response and an RSV A and B cross protection, and exhibiting the least possible risk of immunopathologies associated with the production of Th2-type cytokines.

In addition, for vaccines intended for newborn babies, it is also desirable for the antigen used to exhibit negative immediate hypersensitivity (or IHS). Type I immediate or anaphylactic hypersensitivity to IgE, according to the Gell and Coombs classification, includes the clinical manifestations observed during certain respiratory, ocular, skin, digestive conditions, etc. It is possible to correlate a positive IHS response with a Th2-type response with production of IL-5 and of IgE; thus, in order to reduce the risk of pathologies associated with immunization against RSV, it is desirable not to induce, by virtue of the immunizing molecule, a Th2-type response.

It has also been noted by the inventors that the production of peptides derived from the G protein poses multiple problems, in particular in terms of the formation of disulfide bridges, which must be in the same configuration as that of the native G protein. As a result, the native pairing between the disulfide bridges must be respected while at the same time conserving a good yield.

Thus, the object of the present invention is to obtain novel peptides derived from the G protein which satisfy the problems mentioned above, which are easy to produce industrially and which make it possible to obtain an immune response along with sufficient protection, RSV A and B cross protection, and the least possible risk of immunopathologies, and which in particular exhibit a negative IHS.

Surprisingly, it has been demonstrated that an immunogenic peptide derived from the G protein of RSV subgroup A or B comprising at least:

a first peptide derived from the G protein of RSV subgroup A or B comprising at least at position 173, 176, 182 and 186 a cysteine, and the C-terminal end of which comprises at most the amino acid at position 192; and a second peptide derived from a protein of RSV subgroup A or B, said second peptide being located downstream of said first peptide, such that the immunogenic peptide produced exhibits a disulfide bridge connecting residues 173 and 186 and a second disulfide bridge connecting residues 176 and 182, satisfies the problems mentioned above.

Thus, a subject of the present invention is an immunogenic peptide derived from the G protein of RSV subgroup A or B comprising at least:

a first peptide derived from the G protein of RSV subgroup A or B comprising at least at position 173, 176, 182 and 186 a cysteine, and the C-terminal end of which comprises at most the amino acid at position 192; and a second peptide derived from a protein of RSV subgroup A or B, said second peptide being located downstream of said first peptide, such that the immunogenic peptide produced exhibits a disulfide bridge connecting residues 173 and 186 and a second disulfide bridge connecting residues 176 and 182.

The term "immunogenic peptide" is intended to denote any peptide which, when it is associated with a carrier or an adjuvant, is capable of generating or increasing an immune response directed against RSV. Preferably, this immunogenic peptide also makes it possible to obtain RSV A and B cross protection.

It should be understood that, when said second peptide is chosen from the peptides derived from the RSV G protein, this said second peptide is not a peptide which is naturally contiguous downstream of said first peptide in the sequence of said G protein, in order to avoid picking out an immunogenic peptide the sequence of which would be naturally included in the wild-type sequence of said G protein or in that of one of its natural variants. In fact, these sequences, already described in the documents of the prior art mentioned above, do not make it possible to obtain both the formation and the configuration of the expected disulfide bridges (see below) and a negative IHS.

In the present invention, the term "peptide" will also be intended to denote polypeptides.

The term "located downstream of said first peptide" should be understood to mean that the second peptide is located in the 3' position relative to the first peptide.

The expression peptide "comprising at least at position 173, 176, 182 and 186 a cysteine, and the C-terminal end of which comprises at most the amino acid at position 192" is intended to denote any peptide exhibiting at least 4 cysteines in the same configuration as the native G protein. The position numbers refer to the native G protein of RSV and do not mean that the first peptide according to the invention necessarily comprises all 192 amino acids of the native protein, but that this peptide is a peptide of sequence n-m, with n=1-172 and m=187-192.

The expression "the G protein of RSV subgroup A or B" is intended to denote the envelope protein of RSV A or B.

Preferably, the peptide according to the invention is synthesized in a single block, i.e. it is in fact a single peptide which can be considered as the assembly of a first and a second peptide as defined above.

These two peptides can also be coupled. The coupling is preferably covalent coupling, which can be carried out chemically or by recombinant DNA techniques.

This peptide can in particular be obtained by conventional chemical peptide synthesis, preferably without glycosylation steps, known to those skilled in the art, or via the recombinant pathway, preferably without glycosylation.

The methods for preparing glycosylated, or preferably nonglycosylated, recombinant peptides are today well known to those skilled in the art and will not be developed in the present description. Among the cells which can be used for producing these recombinant proteins, mention may in particular be made of bacterial cells (Olins P. O. and Lee S. C., Curr. Op. Biotechnology, 4:520-525, 1993), and more particularly *E. coli*.

The present invention also relates to an immunogenic peptide derived from the G protein of RSV subgroup A or B of sequence exhibiting, after optimal alignment, at least 80% homology, preferably 85%, 90%, 95% and 99%, with the peptide sequence of the peptide according to the invention.

The expression "amino acid sequence exhibiting at least 80% homology, after optimal alignment, with a given amino acid or nucleic acid sequence" is intended to denote a sequence which, after optimal alignment with said given sequence, comprises a percentage identity of at least 80% with said given sequence.

For the purpose of the present invention, the term "percentage identity" between two amino acid sequences is intended to denote a percentage of amino acid residues which are identical between the two sequences to be compared, obtained after the best alignment, this percentage being purely statistical and the differences between the two sequences being distributed randomly and over their entire length. Sequence comparisons between two amino acid sequences are conventionally carried out by comparing these sequences after having optimally aligned them, said comparison being carried out by segments or by "window of comparison" in order to identify and compare local regions of sequence similarity. The optimal alignment of the sequences for the comparison can be carried out, besides manually, by means of the local homology algorithm of Smith and Waterman (1981) [Ad. App. Math. 2:482], by means of the local homology algorithm of Neddleman and Wunsch (1970) [J. Mol. Biol. 48:443], by means of the similarity search method of Pearson and Lipman (1988) [Proc. Natl. Acad. Sci. USA 85:2444], by means of computer programs using these algorithms (GAP, BESTFIT, FASTA and TFASTA in the Wisconsin Genetics Software Package, Genetics Computer Group, 575 Science Dr., Madison, Wis., or else with the comparison programs BLAST N or BLAST P).

The percentage identity between amino acid sequences is determined by comparing these two optimally aligned sequences by window of comparison in which the region of the nucleic acid or amino acid sequence to be compared may comprise additions or deletions relative to the reference sequence for optimal alignment between these two sequences. The percentage identity is calculated by determining the number of identical positions for which the amino acid residue is identical between the two sequences, dividing this number of identical positions by the total number of positions in the window of comparison, and multiplying the result obtained by 100 so as to obtain the percentage identity between these two sequences.

For example, use may be made of the BLAST program "BLAST 2 sequences", (Altschul et al., Nucl. Acis Res. (1977) 25:3389-3402) the parameters used being those given by default (in particular for the parameters "open gap penalty": 5, and "extension gap penalty": 2; the matrix chosen being for example the "BLOSUM 62" matrix proposed by the program), the percentage identity between the two sequences to be compared being calculated directly by the program.

Among said sequences exhibiting at least 80% homology, preference is given to the peptide sequences capable of inducing an immune response directed against RSV, such as the induction of an immune response measured by means of the standard techniques described in the examples below.

In a preferred embodiment of the invention, the C-terminal end of said first peptide comprises at most the amino acid at position 190.

In another preferred embodiment of the invention, said first peptide exhibits a sequence chosen from the sequence of the G protein of RSV subgroup A or B 130-190, 130-192, 140-190, 140-192, 145-190, 145-192, 148-190, 148-192, 130-188, 140-188, 145-188 or 148-188 and preferably the sequence 140-190.

In another preferred embodiment of the invention, said second peptide consists of a chain of at least 5 amino acids, preferably 6, 7, 8, 9 and 10 amino acids.

In fact, as has been demonstrated in the examples below, it is necessary for the fragment of the immunogenic peptide according to the invention contiguous with position 186 of said first peptide to comprise at least more than 4 amino acids in order for there to be the expected disulfide bridge formation and configuration.

In another preferred embodiment of the invention, said second peptide contains at least one B epitope of RSV A or B. This peptide may in particular be derived from the RSV G or F protein.

In another preferred embodiment of the invention, said second peptide is chosen from the fragments of the RSV G protein comprising at least the fragment 144-158 of the RSV G protein, the C-terminal end of said second peptide comprising at most the amino acid at position 172.

Thus, said second peptide can, in a preferred embodiment of the invention, exhibit a sequence chosen from the sequence 144-158, 144-159 of the RSV G protein and from the described neutralizing peptides of the F protein (described by Trudel et al., J. Gen. Virol., 68:2273-2280, 1987; Trudel et al., Can. J. Microbiol. 33:933-938, 1987; Lopez et al., J. Virol., 64:927-930, 1990 and Scopes et al., J. Gen. Virol., 71:53-59, 1990) such as the peptides of sequence 221-237, 274-287, 262-268 and 483-488 of the RSV F protein.

In a preferred embodiment, said second peptide exhibits the sequence 144-158 or 144-159 of the RSV G protein.

Particularly preferably, said immunogenic peptide derived from the G protein of RSV subgroup A or B exhibits a negative IHS.

As an example of preferred peptides according to the invention, mention may be made of the immunogenic peptides consisting of a first peptide exhibiting a sequence chosen from the sequence of the G protein of RSV subgroup A or B 140-190 or 140-192 and of a second peptide exhibiting a sequence chosen from the sequence 144-158 or 144-159 of the RSV G protein.

Thus, a subject of the present invention is also the peptides of sequences SEQ ID No. 1 (called G20a), SEQ ID No.2 (called G20aP) and SEQ ID No.3 (called G23a).

The invention also relates to the nucleic acid sequences encoding a peptide according to the invention, such as those described above.

A subject of the invention is also a pharmaceutical composition, characterized in that it comprises, in a pharmaceutically acceptable medium, at least one peptide according to the invention or a nucleic acid sequence encoding such a peptide.

These compositions according to the invention may also contain at least one carrier protein and/or an adjuvant.

The carrier protein can advantageously be chosen from the TT (tetanus toxoid) protein, the DT (diphtheria toxoid) protein, the Streptococcal human serum albumin-binding protein and its fragments, cholera toxin (CT) or its B subunit (CTB), *E. coli* enterotoxin (LT) or its B subunit (LTB) and extracts of bacterial membrane proteins such as *Neisseria meningitidis* OMPC (Vella et al., Infect. Immun., 60: 4977-4983, 1992), *Escherichia coli* TraT (Croft et al., J. Immunol., 146:793-798, 1991) or *Neisseria meningitidis* PorB (Fusco et al., J. Infect. Dis., 175:364-372, 1997) or any other protein exhibiting a Th epitope.

One of the preferred carrier proteins consists of an OmpA of a bacterium of the *Klebsiella* genus, which is a major protein of the outer membrane called P40, exhibiting carrier protein activity, systemically, for peptide subunit antigens (WO 95/27787 and WO 96/14415; Haeuw et al., Eur. J. Biochem., 255:446-454, 1998; Plotnicky-Gilquin et al., J. Virol., 73:5637-5645, 1999).

The amino acid sequence of the P40 protein is, for example, identified in the sequence listing of document WO 99/49892 by the sequence SEQ ID No.1.

Another particularly preferred carrier consists of atoxic derivatives of the DT (diphtheria toxoid) protein, in which at least one cysteine residue has been deleted. As an example of such a carrier, mention may be made of the proteins of sequences SEQ ID No.4 (called DTa), SEQ ID No.5 (called DTb) and SEQ ID No. 6 (called DTaDTb).

The adjuvant may in particular be chosen from MPL-A (monophosphoryl lipid A), MF-59, Quil-A (saponin-derived adjuvant), ISCOM (ImmunoStimulating COMplex), dimethyldioctadecylammonium bromide (DDAB) or dimethyldioctadecyl-ammonium chloride (DDAC), alumina (aluminum hydroxide), adjuphos, CpGs (oligodeoxynucleotides containing a specific unit centered on a CpG dinucleotide), Leif (Leishmania-derived protein antigen capable of stimulating PBMC cells and antigen-presenting cells, and of producing a cytokine reaction of the Th-1 type), CT (cholera toxin), LT (heat-labile toxin) and detoxified versions of CT or LT, and from any mixture of these various adjuvants.

The peptide according to the invention may be associated, in particular by coupling, with the carrier protein.

The coupling is preferably covalent coupling, which can be carried out chemically or by recombinant DNA techniques.

In a particular embodiment of the invention, one or more binding elements is (are) introduced into the peptide according to the invention and/or into said carrier in order to facilitate the chemical coupling, said binding element introduced is preferably an amino acid.

According to the invention, it is possible to introduce one or more binding elements, in particular amino acids, in order to facilitate the coupling reactions between the peptide according to the invention and the carrier. The covalent coupling between the peptide according to the invention and said carrier can be carried out at the N- or C-terminal end of said peptide. The bifunctional reagents for this coupling will be determined as a function of the end of said peptide chosen to effect the coupling and of the nature of said carrier to be coupled.

In another particular embodiment, the coupling between the peptide according to the invention and said carrier is carried out by genetic recombination, when said carrier is peptide in nature.

The conjugates derived from a coupling between the peptide according to the invention and said carrier can be prepared by genetic recombination. The chimeric or hybrid protein (conjugate) can be produced by recombinant DNA techniques by insertion into or addition to the DNA sequence encoding said peptide according to the invention of a sequence encoding said carrier which is protein in nature.

The processes for synthesizing the hybrid molecules encompass the methods used in genetic engineering to construct hybrid polynucleotides encoding desired polypeptide sequences. Reference may, for example, advantageously be made to the technique for obtaining genes encoding fusion proteins described by D. V. Goeddel (Gene expression technology, Methods in Enzymology, Vol. 185, 3-187, 1990).

As an example of conjugates, mention may be made of the conjugates of the peptides according to the invention with derivatives of the DT (diphtheria toxoid) protein, in which at least one cysteine residue has been deleted. Such conjugates, which are also part of the invention, are in particular the peptides of sequences SEQ ID No.7 (called G20a-DTa), SEQ ID No.8 (called G20a-DTb) and SEQ ID No.9 (called G20a-DTaDTb).

According to one of the aspects of the invention, the peptide according to the invention is conjugated to the carrier protein via a binding protein; this binding protein may in particular be chosen from a mammalian serum albumin receptor and the receptors present at the surface of mucosal cells.

A subject of the invention is also the composition according to the invention, characterized in that said pharmaceutical composition also comprises at least a second antigen, immunogen or hapten of RSV and/or an antigen, immunogen or hapten derived from a microorganism responsible for pathologies of the airways, chosen from parainfluenza viruses (PIV 1, 2, 3 and 4), influenza virus (A and B), hantaviruses, streptococci, pneumococci, *hemophilus influenza* type b, rhinoviruses, coronaviruses and meningococci.

The term "immunogen, antigen or hapten" is intended to denote in particular any compound expressed by an infectious agent, or one of their structural analogs, which alone or in combination with an adjuvant or carrier is capable of inducing an immune response specific for said infectious agent.

The term "immunogen, antigen or hapten" is also intended to denote in the present description a compound exhibiting structural analogy with said antigen or hapten capable of inducing an immunological response directed against said antigen or hapten in an organism preimmunized with said analogous compound.

In an even more preferred embodiment of the invention, said second antigen of RSV comprises at least one fragment of the respiratory syncytial virus G protein, said fragment comprising a T epitope or being made up of only said T epitope.

In another preferred embodiment of the invention, said second antigen of RSV comprises at least one fragment of the respiratory syncytial virus F protein, said fragment comprising a T epitope or being made up of only said T epitope.

For the purpose of the present invention, the pharmaceutically acceptable medium is the medium in which the compounds of the invention are administered, preferably a medium injectable in humans. It may consist of water, of a saline aqueous solution or of an aqueous solution based on dextrose and/or on glycerol.

The invention also comprises a composition according to the invention, characterized in that said pharmaceutical composition is vehiculed in a form which makes it possible to improve its stability and/or its immunogenicity; thus, it may be vehiculed in the form of liposomes, virosomes, nanospheres, microspheres or microcapsules.

The subject of the invention is also monoclonal or polyclonal antibodies directed against the peptides according to the invention.

The monoclonal antibodies are preferably humanized and produced by the recombinant pathway. According to another aspect of the invention, they are obtained by the phage library method.

Preferably, the monoclonal antibody, the polyclonal antibody or one of their fragments is characterized in that it is capable of binding specifically to an epitope or determinant of the nonglycosylated peptides according to the invention.

The monoclonal antibodies may advantageously be prepared from hybridomas according to the technique described by Kohler and Milstein in 1975 (Nature, 256:495-497, 1975).

The polyclonal antibodies may be prepared, for example, by immunizing an animal, in particular a mouse or a rabbit, with the peptide according to the invention combined with an adjuvant for the immune response, and then purifying the specific antibodies contained in the serum of the immunized animals on an affinity column to which said peptide which served as antigen has been attached beforehand.

The antibodies of the invention also comprise any fragment of said monoclonal antibody capable of binding to an epitope of the peptide according to the invention to which the monoclonal or polyclonal antibody from which said fragment is derived binds. Examples of such fragments include in particular single-chain monoclonal antibodies or Fab or Fab' monovalent fragments and divalent fragments such as F(ab')2, which have the same binding specificity as the monoclonal or polyclonal antibody from which they are derived. A fragment according to the invention may also be a single-chain Fv fragment produced by methods known to those skilled in the art and as described, for example, by Skerra et al. (Science, 240:1038-1041, 1988) and King et al. (Biochemical J., 290: 723-729, 1991).

According to the present invention, fragments of monoclonal or polyclonal antibodies of the invention can be obtained from the monoclonal or polyclonal antibodies as described above by methods such as digestion with enzymes, for instance pepsin or papain, and/or by cleavage of disulfide bridges by chemical reduction. Alternatively, the fragments of monoclonal or polyclonal antibodies included in the present invention may be synthesized by automatic peptide synthesizers such as those provided by the company Applied Biosystems, etc., or may be prepared manually using techniques known to those skilled in the art and as described, for example, by Geysen et al. (J. Immunol. Methods, 102:259-274, 1978).

In general, for the preparation of monoclonal or polyclonal antibodies or their fragments, reference may be made to the techniques which are in particular described in the manual "Antibodies" (Harlow et al., Antibodies: A Laboratory Manual, Cold Spring Harbor Publications pp. 726, 1988) or to the technique for preparation from hybridomas described by Kohler and Milstein in 1975.

The humanized monoclonal antibodies according to the invention or their fragments can be prepared by techniques known to those skilled in the art (Carter et al., PNAS 89:4285-4289, 1992; Mountain et al., Biotechnol. Genet. Eng. Rev., 10:1-142, 1992).

Such humanized monoclonal antibodies according to the invention are preferred for their use in therapeutic methods.

The antibodies of the invention, or their fragments, may also be labeled by labeling of the enzymatic, fluorescent or radioactive type.

The labeled monoclonal antibodies according to the invention, or their fragments, include for example "immunoconjugated" antibodies which can be conjugated, for example, with enzymes such as peroxidase, alkaline phosphatase, β-D-galactosidase, glucose oxidase, glucose amylase, carbonic anhydrase, acetyl-cholinesterase, lysozyme, malate dehydrogenase or glucose-6 phosphate dehydrogenase or with a molecule such as biotin, digoxigenin or la 5-bromodeoxyuridine. Fluorescent labels can also be conjugated to the monoclonal antibodies or their fragments of the invention, and include in particular fluorescein and its derivatives, rhodamine and its derivatives, GFP (green fluorescent protein), dansyl, umbelliferone, etc. In such conjugates, the monoclonal antibodies of the invention or their fragments can be prepared by methods known to those skilled in the art. They can be coupled to the enzymes or to the fluorescent labels directly or via a spacer group or a binding group such as polyaldehyde, for instance glutaraldehyde, ethylenediaminetetraacetic acid (EDTA) or diethylenetriaminepentaacetic acid (DPTA), or in the presence of coupling agents such as periodate, etc. The conjugates comprising labels of fluorescein type can be prepared by reaction with an isothiocyanate.

Other conjugates can also include chemiluminescent labels such as luminol and dioxetanes or bioluminescent labels such as luciferase and luciferin.

Among the labels which can be attached to the monoclonal antibody or one of its fragments according to the invention, preference is also given to radioactive labels such as $^{14}C$, $^{36}Cl$, $^{57}Co$, $^{58}Co$, $^{51}Cr$, $^{152}Eu$, $^{59}Fe$, $^{3}H$, $^{125}I$, $^{131}I$, $^{32}P$, $^{33}P$, $^{35}S$, 75SE and $^{99m}Tc$, which can be detected by known means such as, for example, a gamma counter or a scintillation counter or by autoradiography.

The peptides and/or the antibodies according to the invention, or a nucleic acid sequence encoding such a peptide, can, according to an embodiment of the invention, form part of the composition of a diagnostic kit.

The peptides and the antibodies according to the invention can be used as a medicinal product, and more particularly for preparing a composition intended for the preventive or curative treatment of disorders caused by RSV subgroup A or B.

Thus, the invention also relates to the use of a peptide according to the invention as defined above, or of a nucleic acid sequence encoding such a peptide, for preparing a pharmaceutical composition, preferably a vaccine, intended for the prophylactic or therapeutic treatment of conditions caused by RSV, subgroup A or B, which exhibits an immunogenic response, RSV A and B cross protection and a negative IHS and which does not induce immunopathologies.

A subject of the invention is also the use of a peptide according to the invention as defined above, or of a nucleic acid sequence encoding such a peptide, for preparing a pharmaceutical composition which is intended to generate or increase an immune response against RSV and which does not induce immunopathologies.

The figure legends and examples are intended to illustrate the invention without in any way limiting the scope thereof.

In these examples, reference will be made to the following figures:

FIGS. 1A and 1B: Anti-RSV titer before and after immunization in naive mice (expressed as log 10).

FIGS. 2A and 2B: Anti-RSV titer before and after immunization in mice seropositive with respect to RSV-A (expressed as log 10).

FIGS. 3A and 3B: Anti-RSV titer before and after immunization in mice seropositive with respect to RSV-B (expressed as log 10).

FIGS. 4A and 4B: Protection against an RSV-A challenge in mice immunized with G23 or G20.

FIGS. 5A and 5B: Measurement of granular-type cell infiltrations (followed using the label RB6-8C5) and measurement of Th2 type cytokines (IL-10 and IL-5).

EXAMPLE 1

Production of the G20a Peptide

By way of example, the gene encoding G20a, obtained by PCR, was cloned into an expression vector, the promoter of which is based on the tryptophan (Trp) operon. This results in the vector called pTEXG20a, the DNA of the insert of which was verified by DNA sequencing. The vector was transformed into an *Escherichia coli* K12 bacterium called ICONE®.

A. Fermentation: A 30 1 fermenter (CHEMAP CMF400) containing 18 l of minimum culture medium (g/l) ($KH_2PO_4$, 6/$K_2HPO_4$, 4/$Na_3$ citrate $2H_2O$, 9/yeast extract 1/$(NH_4)_2SO_4$, 5/$CaCl_2$, 0.3/$MgSO_4$,$7H_2O$, 2/glycerol 100) and trace elements (1 ml/l) and Struktol antifoaming agent (0.4 ml/l) supplemented with a solution of tetracycline and tryptophan at a final concentration, respectively, of 0.008 g/l and 0.3 g/l, is inoculated with 1 400 ml of the same medium derived from a preculture of recombinant *E. coli* described above, in a 2 liter fermenter. In batch culture, these physicochemical parameters are kept constant: temperature at 37° C., pH at 7 regulated with $NH_4OH$, stirring 500-1 000 rpm so as to maintain the dissolved $O_2$ level at 30%. When the optical density (OD 620 nm) of the culture medium reaches approximately the value of 50, the expression of the recombinant protein can then be induced by adding 2 ml/liter of culture of a solution of 3-indoleacrylic acid (IAA) at 12.5 g/l. A few hours later, the fermentation is stopped by cooling to 4° C. after depletion of carbon-based substrate (measured by an enzyme assay of the glycerol in the culture medium). The bacterial biomass is obtained by continuous centrifugation of the medium (14 000 rpm, flow rate 100 l/h). The biomass yield is approximately 38 g of dry cells/l.

B. Extraction: The biomass (approximately 500 g of dry cells) is taken up in 10 l of TST buffer (25 mM Tris HCl pH 8, 5 mM $MgCl_2$ $6H_2O$, 2 mM EDTA). The bacterial suspension is ground with a Manton-Gaulin device (3 cycles at 560 bar). Since the G20a recombinant protein is mostly soluble, the purification can be carried out directly from the ground suspension. The G20a can, for example, be captured by expanded bed ion exchange chromatography (Streamline, Pharmacia). Two or three additional chromatography steps (ion exchange and exclusion) are necessary in order to remove the DNA and protein contaminants of the host cell. The purified proteins are analyzed on an SDS-PAGE gel under reduced conditions, on the MINI PROTEAN II SYSTEM device (BioRads). They can be visualized with Coomassie brilliant blue R250.

EXAMPLE 2

Comparison of the Production of the G20a Peptide Compared to the Production of the G7a Peptide A. Synthesis and Characterization of the G7a Peptide (33 Amino Acids)

The G7a peptide (also called "G7") is a fragment of the G protein of RSV-A (158-190) of 33 amino acids. It comprises 4 cysteines at position 173, 176, 182 and 186, capable of forming 2 disulfide bridges. The sequence of the G7 peptide is as follows (SEQ ID No.11):

$K_{158}PNNDFHFEVFNFVPC_{173}SIC_{176}SNNPTC_{182}WAIC_{186}KRIP_{190}$.

The peptide is obtained using an automatic solid-phase peptide synthesizer (SPPS) with Fmoc/tBu chemistry starting from the C-terminal side to the N-terminal side on a scale of 0.25 mmol using the following protected amino acids: Fmoc-L-Ala, Fmoc-L-Arg(Pmc), Fmoc-L-Asn(Trt), Fmoc-L-Asp (OtBu), Fmoc-L-Cys(Trt), Fmoc-L-Glu(OtBu), Fmoc-L-His (Trt), Fmoc-L-Ile, Fmoc-L-Lys(Boc), Fmoc-L-Phe, Fmoc-L-Pro, Fmoc-L-Ser(tBu), Fmoc-L-Thr(tBu), Fmoc-L-Trp, Fmoc-L-Val, Fmoc-L-Pro resin).

1.750 mg of peptide-resin are obtained at the end of synthesis. Half of the sample (890 mg) is cleaved in a solution containing trifluoroacetic acid and also scavenger (1% of TIS) and then lyophilized with a yield of 50% of unpurified reduced peptide.

81 mg of reduced crude peptide are solubilized in 64 ml of water mixed with 16 ml of DMSO (oxidizing solvent) at ambient temperature for 5 days. The oxidation of the crude mixture results in the formation of 2 oxidized forms, numbered ox1 and ox2 according to the order of elution in HPLC (high pressure liquid chromatography) and distinct from the reduced form by HPLC. The oxidized nature of the 2 forms is confirmed by mass spectrometry (4 RSH=>2 RS-S-R minus 4 units of atomic mass; mass of the reduced peptide: 3842.43 Da; mass of the oxidized peptide: 3838.43 Da).

The 2 main peaks observed by RP-HPLC (reverse phase-high pressure liquid chromatography) in the complex mixture thus obtained are isolated and analyzed by mass spectrometry (ES-MS, "ElectronSpray-Mass Spectrometry"). The measured masses obtained are compatible with theoretical masses corresponding to oxidized forms of the G7a peptide (G7ox1: 1.3 mg, i.e. 1.6% yield); RP-HPLC(RT): 13.70 min.; ES-MS: calculated mass=3838.43 Da/measured mass: 3838.27 Da±0.10 and G7ox2: 1.2 mg, i.e. 1.5% yield); RP-HPLC (RT): 15.00 min; ES-MS: calculated mass=3838.43 Da/measured mass: 3838.27 Da±0.10).

Four cysteines (numbered from 1 to 4 from the N-terminal side to the C-terminal side) in a protein can pair according to 3 theoretical isomers: 1-2/3-4,1-3/2-4 and 1-4/2-3. Chemical methods for obtaining and characterizing the 3 theoretical isomers of the G4a hexadecapeptide, corresponding to the central region 172-187 of the RSV-A G protein have been described (Beck et al., J. Pept. Res., 55:24, 2000). The native pairing of the G protein is the 1-4/2-3 form for bovine RSV (Langedijk et al., J. Gen. Virol., 77:1249, 1996) and for human RSV (Beck et al., J. Pept. Res., 55:24, 2000). The pairing of the 4 cysteines of the 2 oxidized forms of the G7a peptide is studied by LC-MS (liquid chromatography-mass spectrometry) and by microsequencing of fragments obtained subsequent to cleavage with thermolysin. The interpretation of the fragments obtained is described in table 1 below.

ylchromane-6 sulfonyl (Pmc) for Arg. The cysteines used possessed the following orthogonal protective groups: Trt for Cys 176 and 182, firstly, and acetamidomethyl (Acm) for Cys 173 and 186. At the end of synthesis, 1 000 mg of the 2 500 mg of peptide-resin were cleaved with a mixture of TFA/EDT/ thioanisole/phenol/TIS/H$_2$O: 20 ml/0.25 ml/1 ml/1.5 g/0.22 ml/1 ml. After reaction for 3 hours with stirring at ambient temperature, the mixture is filtered in order to remove resin and the crude peptide is precipitated by adding cold diethyl

TABLE 1

Peptide map (thermolysin) of the purified G7a-ox2 peptide

| UV peak | Measured mass | Theoretical mass | Interpretation | Attribution |
|---|---|---|---|---|
| 4 | 247.5 (MH+) | 246.3 | FE | |
|   | 280.5 (MH+) | 279.3 | FN | |
|   | 379.6 (MH+) | 378.3 | VFN | |
| 6 | 849.6 (MH+) | 848.9 | ICSNNPTC | 2-3 |
| 7 | 276.5 (MH+) | 275.3 | WA | |
| 12 | 1048.23 ± 0.65 | 1841.1 | ICS ICKRIP | 2-4 |
|   | | 1373.2 | 1373.6 | ICSNNP ICKRIP | 2-4 |
|   | | 1475.8 | 1474.8 | ICSNNPT ICKRIP | 2-4 |
| 14 | 1279.28 ± 0.46 | 1278.6 | FVPCS ICKRIP | 1-4 |
| 16 | 1035.01 ± 0.21 | 1035.2 | ICSNNPTCW | 2-3 |
| 17 | 1106.41 ± 0.83 | 1106.3 | ICSNNPTCWA | 2-3 |
| | Conclusion: G7a-ox2 = G7a 1-4/2-3 + G7a 1-3/2-4 | | KPNNDFHFEVFNFVPCSICSNNPTCWAICKRIP | 1-4/2-3 |
| | | | KPNNDFHFEVFNFVPCSICSNNPTCWAICKRIP | 1-3/2-4 |

It appears that the G7ox2 peptide is a mixture, which is unseparable by HPLC, of the peptides G7(1-4/2-3) and G7(1-3/2-4) in unknown proportion. The yield from the reaction and from the purification is very low (1.5%).

B. Synthesis and Characterization of the G20a Peptide (69 Amino Acids)

The G20a peptide is a fragment of the G protein of RSV-A (140-190)-(144-158) of 69 amino acids. It comprises 4 cysteines capable of forming 2 disulfide bridges. The sequence of the G20a peptide is as follows (SEQ ID No.1):

MEFQ$_{140}$TQPSKPTTKQRQNKPPNKPNNDFHFEVFN FVPC$_{173}$SIC$_{176}$SNNPT C$_{182}$WAIC$_{186}$KRIP$_{190}$S$_{144}$ KPTT-KQRQNKPPNK$_{158}$.

The G20a peptide is obtained by automatic solid-phase synthesis with Fmoc/tBu chemistry on a scale of 0.25 mmol using a hydroxymethylphenoxymethyl (HMP) resin preloaded with a Lys (Boc) (0.70 mmol/g) and Fmoc-amino acids protected on the side chains with the following groups: trityl (Trt) for Asn, Gln and His; tert-butyl ether (tBu) for Ser and Thr; tert-butyl ester (OtBu) for Asp and Glu, tert-butyloxycarbonyl (Boc) for Lys and Trp and 2,2,5,7,8-pentamethether. The precipitate is solubilized in a mixture of H$_2$O/ CH$_3$CN/TFA:80/20 /0.1:v/v/v, and then lyophilized.

Before oxidation, the crude peptide is purified by RP-HPLC using a water/aceto-nitrile gradient and analyzed by RP-HPLC (RP-HPLC purity >75%; yield: 38%) and ES-MS (calculated mass: 8186.42 Da/measured mass: 8186.40).

Disulfide bridge formation in 2 steps: In order to form the bridge between Cys 176 and Cys 182, which are unprotected, the lyophilized peptide is solubilized (1 mg/ml) in a mixture of DMSO-H$_2$O at 20% (v/v) and stirred at ambient temperature for 4 hours (Tam et al., J. Am. Chem. Soc., 113:6657, 1991). At the end of the reaction, in order to eliminate the DMSO, the peptide is purified by RP-HPLC under the same conditions as the reduced peptide. The fractions corresponding to the main peak are collected and lyophilized. An aliquot is subjected to analysis by ES-MS in order to verify that the first disulfide bridge has indeed been formed. The second bridge, between Cys(Acm) 173 and 186 is obtained by oxidation with (Buku et al., Int. J. Peptide. Res., 33, 86, 1989 and Annis et al., Meth. Enzymol., 289, 198, 1997). The peptide is solubilized (1 mg/ml) in a mixture of acetic acid/water at 80%

(v/v) and 10% of 1N HCl are added. The solution is saturated with nitrogen. Ten equivalents of iodine solubilized in a mixture of acetic acid/water at 80% (v/v) are then added rapidly and the medium is stirred for 5 hours at ambient temperature. The excess iodine is reduced by the dropwise addition of an aqueous ascorbic acid solution until the characteristic color of the iodine disappears. The crude oxidized peptide is purified by RP-HPLC, lyophilized and analyzed by RP-HPLC and ES-MS.

Disulfide bridge formation in 1 step: A protocol for production in one step was also by direct oxidation with iodine on the reduced peptide also making it possible to obtain the peptide of interest. The yield then goes from 22 to 44% (RP-HPLC purity >90%; calculated mass: 8140.22 Da/measured mass: 8040.30 Da).

The pairing of the disulfide bridges is studied by LC-MS and by microsequencing of the fragments obtained subsequent to cleavage of the peptide with thermolysin. The fragments obtained and the interpretation thereof are described in table 2 below.

TABLE 2

Peptide map (thermolysin) of the G20a peptide.

| UV peak | Measured mass | Theoretical mass | Interpretation | Attribution |
|---|---|---|---|---|
| 29 | 1691.52 ± 0.39 | 1692.1 | FVPCSI ICKRIPSKP | 1-4 |
| 30 | 1591 ± 0.27 | 1591.0 | FVPCS ICKRIPSKP | 1-4 |
| 34 | 1035.49 ± 0.66 | 1035.2 | ICSNNPTCW | 2-3 |
| 35 | 1106.27 ± 0.33 | 1106.3 | ICSNNPTCWA | 2-3 |
| | Conclusion: G20a 1-4/2-3 | | ---FVPCSICSNNPTCWAICKRIPSKPT--- | 1-4/2-3 |

It appears, surprisingly, that the protocol described above makes it possible to obtain only the native form G20a (1-4/2-3).

Thus, the G20a peptide (69 aa) was easier to produce than the G7a peptide (33 aa) despite the fact of adding a further 36 aa step by step. The two-step protocol described for the G20a peptide was applied to the G7a peptide (2% yield) confirming the results reported in example 1. The explanation proposed a posteriori, which is merely a hypothesis and is nonlimiting, is that it is necessary to have more than 4 amino acids on the C-terminal side of Cys 186 in order that the native pairing between, firstly, Cys 173 and Cys 186 and, secondly, Cys 176 and Cys 182 may take place with a good yield and form a structural unit known as a "cystine noose" present in the native G protein (Doreleijers et al., Biochemistry, 35:14684, 1996) and which corresponds to an immunodominant epitope of the RSV G protein (Plotnicky et al., J. Virol., 73:5637, 1999).

This example therefore demonstrates that the addition of a peptide fragment of non-wild-type sequence on the C-terminal side of the conserved region of the 2 disulfide bridges makes it possible to facilitate the synthesis thereof, while at the same time conserving the "cystine noose" structural unit present in the native G protein.

EXAMPLE 3

Immunogenicity and Protection

A. Anti-RSV Titer Before and After Immunization in Naive Mice

In order to test the immunogenicity of the G23a and G20a peptides, Balb/c mice were immunized with 6 or 1.5 µg of G2Na equivalent twice, on D0 and D14, intramuscularly.

The G2Na peptide (also called "G2A" or "G2a") is the aa 130-230 fragment of the G protein of RSV subgroup A as identified, for example, in the sequence listing of application WO 95/27787 by the sequence SEQ ID No. 1.

Some mice were sensitized with RSV 20 days before the first immunization in order to make them seropositive with respect to RSV. A sample was taken from the mice before each immunization and the anti-G2Na, RSV-A and RSV-B antibody titers were determined.

Ten days after the final immunization, the mice were challenged with $10^5$ pfu/50 µl of RSV-A. The viral titer was measured 5 days after the challenge.

Figure 1B:
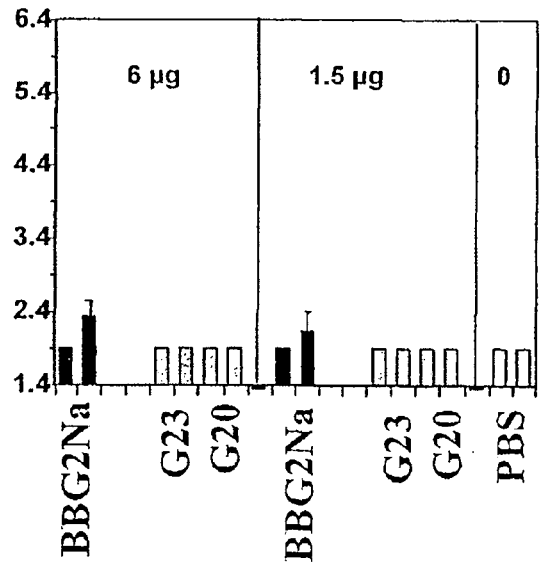

The mice immunized with G20a or G23a develop anti-RSV-A and RSV-B antibody responses from the first immunization (see FIGS. 1A and 1B). An increase is observed after a boost with the various molecules tested (results not shown).

B. Anti-RSV Titer Before and After Immunization in Mice Seropositive with Respect to RSV-A or to RSV-B (Expressed as log 10)

Figure 2A:
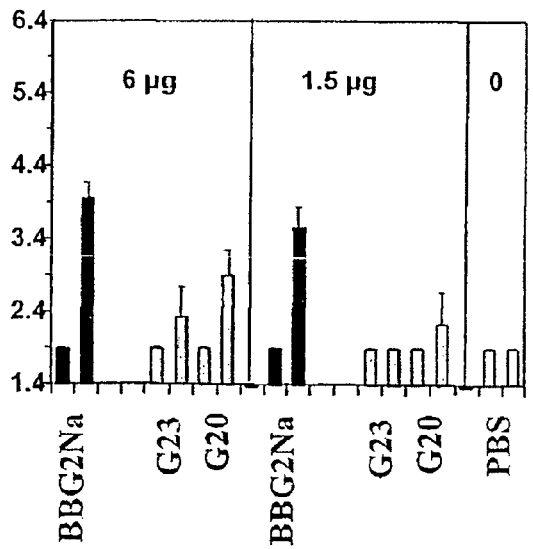
Figure 2B:
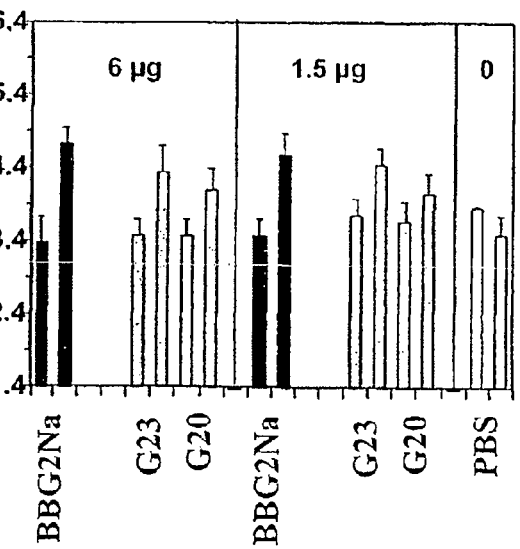

It was noted that the molecules remain immunogenic even in the presence of RSV type A (see FIGS. 2A and 2B) or B (see FIGS. 3A and 3B) antibodies.

C. Protection Against an RSV-A Challenge in Mice Immunized with G23a or G20a

Figures 3A, 3B, 4A, 4B:
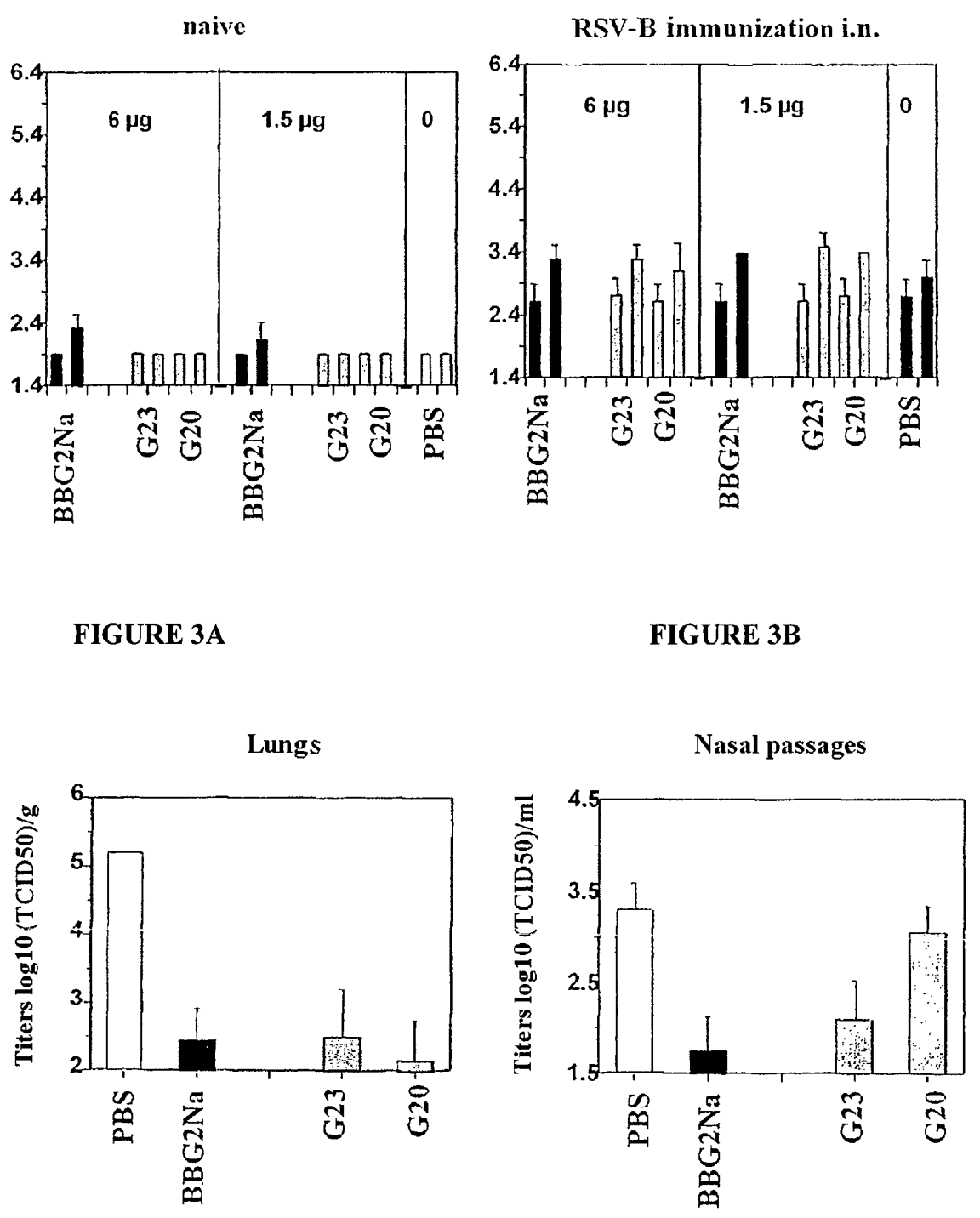

The immunization with G23a or G20a induces protection of the pulmonary tract subsequent to challenge with RSV-A (see FIGS. 4A and 4B).

The results indicate that G23a and G20a are immunogenic and protective in naive mice. In addition, the immunogenicity and the protection observed with these two molecules are comparable to those observed with BBG2Na (the BBG2Na peptide is the peptide resulting from fusion of the G2Na peptide with the "BB" fragment of the streptococcal human serum albumin-binding protein, as defined in application WO 95/27787).

EXAMPLE 4

Determination of the IHS

Guinea pigs are immunized on D0 and D8 with the various molecules adjuvented with 20% (v/v) adjuphos, given i.m. On D21, a booster is given with the various molecules, nonadjuvented, by i.v. The death of the guinea pigs is then evaluated.

A positive experimental control consisting of ovalbumin at 200 μg is included for each molecule tested (cf. table 3 below).

TABLE 3

|      | T+ (OVA) | T−  | 4 mg | 40 mg |
|------|----------|-----|------|-------|
| G20a | 5/6      | 0/6 | 0/6  | 0/6   |

The results indicate that G20 does not induce any IHS in 6/6 animals tested.

EXAMPLE 5

Immunopathologies

The mice are immunized three times with G23a adjuvented with 20% alhydrogel, on D0, D14 and D28. The mice are challenged on D34 with 105 pfu/50 μl of RSV-A. Seven days after the challenge, the lungs are recovered and digested and the cells infiltrating the lungs are analyzed by FACS (Fluorescens Activated Cell Sorter). The cytokines are themselves also analyzed by FACS after overnight incubation with a nonspecific activator. IL-10 and IL-5 are measured.

The results (see FIGS. 5A and 5B) indicate that G23a, whatever the dose tested, does not induce infiltrations of granular-type cells (followed using the label RB6-8C5). On the other hand, FI-RSV (formalin-inactivated RSV), which induces an immunopathology, induces infiltration of this type of cell in the lungs of mice immunized with FI-RSV and challenged with RSV.

Measurement of the Th2-type cytokines (IL-10 and IL-5) indicates that, unlike FI-RSV, no pathology is observed after immunization with G23a.

The invention claimed is:

1. A method of generating and/or increasing an immunogenic response directed against Respiratory Syncytial Virus (RSV) comprising administering to an animal, including a human, an immunogenic peptide derived from the G protein of RSV subgroup A, wherein the immunogenic peptide comprises a sequence selected from the group consisting of the sequences set forth in SEQ ID NO:1, SEQ ID NO:2, and SEQ ID NO:3.

2. The method of claim 1, wherein the immunogenic response is directed against RSV subgroups A and B.

3. The method of claim 1 which does not induce immunopathologies.

4. The method of claim 1 which exhibits negative immediate hypersensitivity.

5. The method of claim 1, wherein the immunogenic peptide is formulated in a pharmaceutically acceptable medium.

6. The method of claim 1, wherein the immunogenic peptide further comprises at least one carrier protein and/or an adjuvant.

7. The method of claim 1, wherein the immunogenic peptide is conjugated to a carrier protein and comprises a sequence selected from the group consisting of the sequences set forth in SEQ ID NO:7, SEQ ID NO:8, and SEQ ID NO:9.

* * * * *

```
SEQUENCE LISTING

<160> NUMBER OF SEQ ID NOS: 26

<210> SEQ ID NO 1
<211> LENGTH: 69
<212> TYPE: PRT
<213> ORGANISM: Artificial sequence
<220> FEATURE:
<223> OTHER INFORMATION: Description of artificial sequence: G20a
      peptide derived from RSV G protein

<400> SEQUENCE: 1

Met Glu Phe Gln Thr Gln Pro Ser Lys Pro Thr Thr Lys Gln Arg Gln
 1               5                  10                  15

Asn Lys Pro Pro Asn Lys Pro Asn Asn Asp Phe His Phe Glu Val Phe
             20                  25                  30

Asn Phe Val Pro Cys Ser Ile Cys Ser Asn Asn Pro Thr Cys Trp Ala
         35                  40                  45

Ile Cys Lys Arg Ile Pro Ser Lys Pro Thr Thr Lys Gln Arg Gln Asn
     50                  55                  60

Lys Pro Pro Asn Lys
 65

<210> SEQ ID NO 2
<211> LENGTH: 70
<212> TYPE: PRT
<213> ORGANISM: Artificial sequence
<220> FEATURE:
<223> OTHER INFORMATION: Description of artificial sequence: G20aP
      peptide derived from RSV G protein

<400> SEQUENCE: 2

Met Glu Phe Gln Thr Gln Pro Ser Lys Pro Thr Thr Lys Gln Arg Gln
 1               5                  10                  15

Asn Lys Pro Pro Asn Lys Pro Asn Asn Asp Phe His Phe Glu Val Phe
             20                  25                  30

Asn Phe Val Pro Cys Ser Ile Cys Ser Asn Asn Pro Thr Cys Trp Ala
```

```
                    35                  40                  45
Ile Cys Lys Arg Ile Pro Ser Lys Pro Thr Thr Lys Gln Arg Gln Asn
         50                  55                  60

Lys Pro Pro Asn Lys Pro
 65                  70

<210> SEQ ID NO 3
<211> LENGTH: 71
<212> TYPE: PRT
<213> ORGANISM: Artificial sequence
<220> FEATURE:
<223> OTHER INFORMATION: Description of artificial sequence: G23a
      peptide derived from RSV G protein

<400> SEQUENCE: 3

Met Glu Phe Gln Thr Gln Pro Ser Lys Pro Thr Thr Lys Gln Arg Gln
 1               5                  10                  15

Asn Lys Pro Pro Asn Lys Pro Asn Asn Asp Phe His Phe Glu Val Phe
                20                  25                  30

Asn Phe Val Pro Cys Ser Ile Cys Ser Asn Asn Pro Thr Cys Trp Ala
            35                  40                  45

Ile Cys Lys Arg Ile Pro Asn Lys Ser Lys Pro Thr Thr Lys Gln Arg
         50                  55                  60

Gln Asn Lys Pro Pro Asn Lys
 65                  70

<210> SEQ ID NO 4
<211> LENGTH: 185
<212> TYPE: PRT
<213> ORGANISM: Artificial sequence
<220> FEATURE:
<223> OTHER INFORMATION: Description of artificial sequence: Dta peptide
      derived from CRM 197 atoxic derivative of the
      diphteric toxin

<400> SEQUENCE: 4

Gly Ala Asp Asp Val Val Asp Ser Ser Lys Ser Phe Val Met Glu Asn
 1               5                  10                  15

Phe Ser Ser Tyr His Gly Thr Lys Pro Gly Tyr Val Asp Ser Ile Gln
                20                  25                  30

Lys Gly Ile Gln Lys Pro Lys Ser Gly Thr Gln Gly Asn Tyr Asp Asp
            35                  40                  45

Asp Trp Lys Glu Phe Tyr Ser Thr Asp Asn Lys Tyr Asp Ala Ala Gly
         50                  55                  60

Tyr Ser Val Asp Asn Glu Asn Pro Leu Ser Gly Lys Ala Gly Gly Val
 65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
         115                 120                 125

Asp Gly Ala Ser Arg Val Val Leu Ser Leu Pro Phe Ala Glu Gly Ser
     130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175
```

```
Ala Met Tyr Glu Tyr Met Ala Gln Ala
            180             185

<210> SEQ ID NO 5
<211> LENGTH: 255
<212> TYPE: PRT
<213> ORGANISM: Artificial sequence
<220> FEATURE:
<223> OTHER INFORMATION: Description of artificial sequence: Dtb peptide
      derived from CRM 197 atoxic derivative of the
      diphteric toxin

<400> SEQUENCE: 5

Ile Asn Leu Asp Trp Asp Val Ile Arg Asp Lys Thr Lys Thr Lys Ile
1               5                   10                  15

Glu Ser Leu Lys Glu His Gly Pro Ile Lys Asn Lys Met Ser Glu Ser
            20                  25                  30

Pro Asn Lys Thr Val Ser Glu Glu Lys Ala Lys Gln Tyr Leu Glu Glu
        35                  40                  45

Phe His Gln Thr Ala Leu Glu His Pro Glu Leu Ser Glu Leu Lys Thr
    50                  55                  60

Val Thr Gly Thr Asn Pro Val Phe Ala Gly Ala Asn Tyr Ala Ala Trp
65                  70                  75                  80

Ala Val Asn Val Ala Gln Val Ile Asp Ser Glu Thr Ala Asp Asn Leu
                85                  90                  95

Glu Lys Thr Thr Ala Ala Leu Ser Ile Leu Pro Gly Ile Gly Ser Val
            100                 105                 110

Met Gly Ile Ala Asp Gly Ala Val His His Asn Thr Glu Glu Ile Val
        115                 120                 125

Ala Gln Ser Ile Ala Leu Ser Ser Leu Met Val Ala Gln Ala Ile Pro
    130                 135                 140

Leu Val Gly Glu Leu Val Asp Ile Gly Phe Ala Ala Tyr Asn Phe Val
145                 150                 155                 160

Glu Ser Ile Ile Asn Leu Phe Gln Val Val His Asn Ser Tyr Asn Arg
                165                 170                 175

Pro Ala Tyr Ser Pro Gly His Lys Thr Gln Pro Phe Leu His Asp Gly
            180                 185                 190

Tyr Ala Val Ser Trp Asn Thr Val Glu Asp Ser Ile Ile Arg Thr Gly
        195                 200                 205

Phe Gln Gly Glu Ser Gly His Asp Ile Lys Ile Thr Ala Glu Asn Thr
    210                 215                 220

Pro Leu Pro Ile Ala Gly Val Leu Leu Pro Thr Ile Pro Gly Lys Leu
225                 230                 235                 240

Asp Val Asn Lys Ser Lys Thr His Ile Ser Val Asn Gly Arg Lys
                245                 250                 255

<210> SEQ ID NO 6
<211> LENGTH: 440
<212> TYPE: PRT
<213> ORGANISM: Artificial sequence
<220> FEATURE:
<223> OTHER INFORMATION: Description of artificial sequence: Fusion
      peptide DtaDTb derived from CRM 197 atoxic derivative of the
      diphteric toxin

<400> SEQUENCE: 6

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
```

-continued

```
                20                  25                  30
Lys Gly Ile Gln Lys Pro Lys Ser Gly Thr Gln Gly Asn Tyr Asp Asp
            35                  40                  45

Asp Trp Lys Glu Phe Tyr Ser Thr Asp Asn Lys Tyr Asp Ala Ala Gly
 50                  55                  60

Tyr Ser Val Asp Asn Glu Asn Pro Leu Ser Gly Lys Ala Gly Gly Val
 65                  70                  75                  80

Val Lys Val Thr Tyr Pro Gly Leu Thr Lys Val Leu Ala Leu Lys Val
                    85                  90                  95

Asp Asn Ala Glu Thr Ile Lys Lys Glu Leu Gly Leu Ser Leu Thr Glu
                100                 105                 110

Pro Leu Met Glu Gln Val Gly Thr Glu Glu Phe Ile Lys Arg Phe Gly
            115                 120                 125

Asp Gly Ala Ser Arg Val Val Leu Ser Leu Pro Phe Ala Glu Gly Ser
            130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Ile Asn Leu Asp Trp Asp Val
                180                 185                 190

Ile Arg Asp Lys Thr Lys Thr Lys Ile Glu Ser Leu Lys Glu His Gly
            195                 200                 205

Pro Ile Lys Asn Lys Met Ser Glu Ser Pro Asn Lys Thr Val Ser Glu
 210                 215                 220

Glu Lys Ala Lys Gln Tyr Leu Glu Glu Phe His Gln Thr Ala Leu Glu
225                 230                 235                 240

His Pro Glu Leu Ser Glu Leu Lys Thr Val Thr Gly Thr Asn Pro Val
                    245                 250                 255

Phe Ala Gly Ala Asn Tyr Ala Ala Trp Ala Val Asn Val Ala Gln Val
                260                 265                 270

Ile Asp Ser Glu Thr Ala Asp Asn Leu Glu Lys Thr Thr Ala Ala Leu
            275                 280                 285

Ser Ile Leu Pro Gly Ile Gly Ser Val Met Gly Ile Ala Asp Gly Ala
290                 295                 300

Val His His Asn Thr Glu Glu Ile Val Ala Gln Ser Ile Ala Leu Ser
305                 310                 315                 320

Ser Leu Met Val Ala Gln Ala Ile Pro Leu Val Gly Glu Leu Val Asp
                325                 330                 335

Ile Gly Phe Ala Ala Tyr Asn Phe Val Glu Ser Ile Ile Asn Leu Phe
                340                 345                 350

Gln Val Val His Asn Ser Tyr Asn Arg Pro Ala Tyr Ser Pro Gly His
            355                 360                 365

Lys Thr Gln Pro Phe Leu His Asp Gly Tyr Ala Val Ser Trp Asn Thr
            370                 375                 380

Val Glu Asp Ser Ile Ile Arg Thr Gly Phe Gln Gly Glu Ser Gly His
385                 390                 395                 400

Asp Ile Lys Ile Thr Ala Glu Asn Thr Pro Leu Pro Ile Ala Gly Val
                405                 410                 415

Leu Leu Pro Thr Ile Pro Gly Lys Leu Asp Val Asn Lys Ser Lys Thr
                420                 425                 430

His Ile Ser Val Asn Gly Arg Lys
            435                 440
```

<210> SEQ ID NO 7
<211> LENGTH: 255
<212> TYPE: PRT
<213> ORGANISM: Artificial sequence
<220> FEATURE:
<223> OTHER INFORMATION: Description of artificial sequence: Fusion
      peptide G20a-DTa derived from RSV G protein and from CRM 197
      atoxic derivative of the diphteric toxin

<400> SEQUENCE: 7

```
Met Glu Phe Gln Thr Gln Pro Ser Lys Pro Thr Thr Lys Gln Arg Gln
 1               5                  10                  15

Asn Lys Pro Pro Asn Lys Pro Asn Asn Asp Phe His Phe Glu Val Phe
                20                  25                  30

Asn Phe Val Pro Cys Ser Ile Cys Ser Asn Asn Pro Thr Cys Trp Ala
            35                  40                  45

Ile Cys Lys Arg Ile Pro Ser Lys Pro Thr Thr Lys Gln Arg Gln Asn
        50                  55                  60

Lys Pro Pro Asn Lys Pro Gly Ala Asp Asp Val Val Asp Ser Ser Lys
65                  70                  75                  80

Ser Phe Val Met Glu Asn Phe Ser Ser Tyr His Gly Thr Lys Pro Gly
                85                  90                  95

Tyr Val Asp Ser Ile Gln Lys Gly Ile Gln Lys Pro Lys Ser Gly Thr
            100                 105                 110

Gln Gly Asn Tyr Asp Asp Asp Trp Lys Glu Phe Tyr Ser Thr Asp Asn
        115                 120                 125

Lys Tyr Asp Ala Ala Gly Tyr Ser Val Asp Asn Glu Asn Pro Leu Ser
    130                 135                 140

Gly Lys Ala Gly Gly Val Val Lys Val Thr Tyr Pro Gly Leu Thr Lys
145                 150                 155                 160

Val Leu Ala Leu Lys Val Asp Asn Ala Glu Thr Ile Lys Lys Glu Leu
                165                 170                 175

Gly Leu Ser Leu Thr Glu Pro Leu Met Glu Gln Val Gly Thr Glu Glu
            180                 185                 190

Phe Ile Lys Arg Phe Gly Asp Gly Ala Ser Arg Val Val Leu Ser Leu
        195                 200                 205

Pro Phe Ala Glu Gly Ser Ser Ser Val Glu Tyr Ile Asn Asn Trp Glu
    210                 215                 220

Gln Ala Lys Ala Leu Ser Val Glu Leu Glu Ile Asn Phe Glu Thr Arg
225                 230                 235                 240

Gly Lys Arg Gly Gln Asp Ala Met Tyr Glu Tyr Met Ala Gln Ala
                245                 250                 255
```

<210> SEQ ID NO 8
<211> LENGTH: 325
<212> TYPE: PRT
<213> ORGANISM: Artificial sequence
<220> FEATURE:
<223> OTHER INFORMATION: Description of artificial sequence: Fusion
      peptide G20a-DTb derived from RSV G protein and from CRM 197
      atoxic derivative of the diphteric toxin

<400> SEQUENCE: 8

```
Met Glu Phe Gln Thr Gln Pro Ser Lys Pro Thr Thr Lys Gln Arg Gln
 1               5                  10                  15

Asn Lys Pro Pro Asn Lys Pro Asn Asn Asp Phe His Phe Glu Val Phe
                20                  25                  30
```

```
Asn Phe Val Pro Cys Ser Ile Cys Ser Asn Asn Pro Thr Cys Trp Ala
        35                  40                  45

Ile Cys Lys Arg Ile Pro Ser Lys Pro Thr Thr Lys Gln Arg Gln Asn
 50                  55                  60

Lys Pro Pro Asn Lys Pro Ile Asn Leu Asp Trp Asp Val Ile Arg Asp
 65                  70                  75                  80

Lys Thr Lys Thr Lys Ile Glu Ser Leu Lys Glu His Gly Pro Ile Lys
                 85                  90                  95

Asn Lys Met Ser Glu Ser Pro Asn Lys Thr Val Ser Glu Glu Lys Ala
            100                 105                 110

Lys Gln Tyr Leu Glu Glu Phe His Gln Thr Ala Leu Glu His Pro Glu
        115                 120                 125

Leu Ser Glu Leu Lys Thr Val Thr Gly Thr Asn Pro Val Phe Ala Gly
130                 135                 140

Ala Asn Tyr Ala Ala Trp Ala Val Asn Val Ala Gln Val Ile Asp Ser
145                 150                 155                 160

Glu Thr Ala Asp Asn Leu Glu Lys Thr Thr Ala Ala Leu Ser Ile Leu
                165                 170                 175

Pro Gly Ile Gly Ser Val Met Gly Ile Ala Asp Gly Ala Val His His
            180                 185                 190

Asn Thr Glu Glu Ile Val Ala Gln Ser Ile Ala Leu Ser Ser Leu Met
        195                 200                 205

Val Ala Gln Ala Ile Pro Leu Val Gly Glu Leu Val Asp Ile Gly Phe
    210                 215                 220

Ala Ala Tyr Asn Phe Val Glu Ser Ile Ile Asn Leu Phe Gln Val Val
225                 230                 235                 240

His Asn Ser Tyr Asn Arg Pro Ala Tyr Ser Pro Gly His Lys Thr Gln
                245                 250                 255

Pro Phe Leu His Asp Gly Tyr Ala Val Ser Trp Asn Thr Val Glu Asp
            260                 265                 270

Ser Ile Ile Arg Thr Gly Phe Gln Gly Glu Ser Gly His Asp Ile Lys
        275                 280                 285

Ile Thr Ala Glu Asn Thr Pro Leu Pro Ile Ala Gly Val Leu Leu Pro
    290                 295                 300

Thr Ile Pro Gly Lys Leu Asp Val Asn Lys Ser Lys Thr His Ile Ser
305                 310                 315                 320

Val Asn Gly Arg Lys
                325

<210> SEQ ID NO 9
<211> LENGTH: 510
<212> TYPE: PRT
<213> ORGANISM: Artificial sequence
<220> FEATURE:
<223> OTHER INFORMATION: Description of artificial sequence: Fusion
      peptide G20a-DTaDTb derived from RSV G protein and from CRM 197
      atoxic derivative of the diphteric toxin

<400> SEQUENCE: 9

Met Glu Phe Gln Thr Gln Pro Ser Lys Pro Thr Thr Lys Gln Arg Gln
 1               5                  10                  15

Asn Lys Pro Pro Asn Lys Pro Asn Asn Asp Phe His Phe Glu Val Phe
             20                  25                  30

Asn Phe Val Pro Cys Ser Ile Cys Ser Asn Asn Pro Thr Cys Trp Ala
         35                  40                  45

Ile Cys Lys Arg Ile Pro Ser Lys Pro Thr Thr Lys Gln Arg Gln Asn
```

-continued

```
            50                  55                  60
Lys Pro Pro Asn Lys Pro Gly Ala Asp Asp Val Asp Ser Ser Lys
 65                  70                  75                  80

Ser Phe Val Met Glu Asn Phe Ser Ser Tyr His Gly Thr Lys Pro Gly
                 85                  90                  95

Tyr Val Asp Ser Ile Gln Lys Gly Ile Gln Lys Pro Lys Ser Gly Thr
                100                 105                 110

Gln Gly Asn Tyr Asp Asp Asp Trp Lys Glu Phe Tyr Ser Thr Asp Asn
                115                 120                 125

Lys Tyr Asp Ala Ala Gly Tyr Ser Val Asp Asn Glu Asn Pro Leu Ser
130                 135                 140

Gly Lys Ala Gly Gly Val Val Lys Val Thr Tyr Pro Gly Leu Thr Lys
145                 150                 155                 160

Val Leu Ala Leu Lys Val Asp Asn Ala Glu Thr Ile Lys Lys Glu Leu
                165                 170                 175

Gly Leu Ser Leu Thr Glu Pro Leu Met Glu Gln Val Gly Thr Glu Glu
                180                 185                 190

Phe Ile Lys Arg Phe Gly Asp Gly Ala Ser Arg Val Val Leu Ser Leu
                195                 200                 205

Pro Phe Ala Glu Gly Ser Ser Ser Val Glu Tyr Ile Asn Asn Trp Glu
                210                 215                 220

Gln Ala Lys Ala Leu Ser Val Glu Leu Glu Ile Asn Phe Glu Thr Arg
225                 230                 235                 240

Gly Lys Arg Gly Gln Asp Ala Met Tyr Glu Tyr Met Ala Gln Ala Ile
                245                 250                 255

Asn Leu Asp Trp Asp Val Ile Arg Asp Lys Thr Lys Thr Lys Ile Glu
                260                 265                 270

Ser Leu Lys Glu His Gly Pro Ile Lys Asn Lys Met Ser Glu Ser Pro
                275                 280                 285

Asn Lys Thr Val Ser Glu Glu Lys Ala Lys Gln Tyr Leu Glu Glu Phe
290                 295                 300

His Gln Thr Ala Leu Glu His Pro Glu Leu Ser Glu Leu Lys Thr Val
305                 310                 315                 320

Thr Gly Thr Asn Pro Val Phe Ala Gly Ala Asn Tyr Ala Ala Trp Ala
                325                 330                 335

Val Asn Val Ala Gln Val Ile Asp Ser Glu Thr Ala Asp Asn Leu Glu
                340                 345                 350

Lys Thr Thr Ala Ala Leu Ser Ile Leu Pro Gly Ile Gly Ser Val Met
                355                 360                 365

Gly Ile Ala Asp Gly Ala Val His His Asn Thr Glu Glu Ile Val Ala
                370                 375                 380

Gln Ser Ile Ala Leu Ser Ser Leu Met Val Ala Gln Ala Ile Pro Leu
385                 390                 395                 400

Val Gly Glu Leu Val Asp Ile Gly Phe Ala Ala Tyr Asn Phe Val Glu
                405                 410                 415

Ser Ile Ile Asn Leu Phe Gln Val Val His Asn Ser Tyr Asn Arg Pro
                420                 425                 430

Ala Tyr Ser Pro Gly His Lys Thr Gln Pro Phe Leu His Asp Gly Tyr
                435                 440                 445

Ala Val Ser Trp Asn Thr Val Glu Asp Ser Ile Ile Arg Thr Gly Phe
                450                 455                 460

Gln Gly Glu Ser Gly His Asp Ile Lys Ile Thr Ala Glu Asn Thr Pro
465                 470                 475                 480
```

```
Leu Pro Ile Ala Gly Val Leu Leu Pro Thr Ile Pro Gly Lys Leu Asp
            485                 490                 495

Val Asn Lys Ser Lys Thr His Ile Ser Val Asn Gly Arg Lys
        500                 505                 510

<210> SEQ ID NO 10
<211> LENGTH: 9
<212> TYPE: PRT
<213> ORGANISM: Artificial sequence
<220> FEATURE:
<223> OTHER INFORMATION: Description of artificial sequence: Peptide
      derived from RSV G protein

<400> SEQUENCE: 10

Ile Cys Lys Arg Ile Pro Asn Lys Lys
 1               5

<210> SEQ ID NO 11
<211> LENGTH: 33
<212> TYPE: PRT
<213> ORGANISM: Artificial sequence
<220> FEATURE:
<223> OTHER INFORMATION: Description of artificial sequence: Peptide
      derived from RSV G protein

<400> SEQUENCE: 11

Lys Pro Asn Asn Asp Phe His Phe Glu Val Phe Asn Phe Val Pro Cys
 1               5                  10                  15

Ser Ile Cys Ser Asn Asn Pro Thr Cys Trp Ala Ile Cys Lys Arg Ile
            20                  25                  30

Pro

<210> SEQ ID NO 12
<211> LENGTH: 8
<212> TYPE: PRT
<213> ORGANISM: Artificial sequence
<220> FEATURE:
<223> OTHER INFORMATION: Description of artificial sequence: Peptide
      derived from RSV G protein

<400> SEQUENCE: 12

Ile Cys Ser Asn Asn Pro Thr Cys
 1               5

<210> SEQ ID NO 13
<211> LENGTH: 6
<212> TYPE: PRT
<213> ORGANISM: Artificial sequence
<220> FEATURE:
<223> OTHER INFORMATION: Description of artificial sequence: Peptide
      derived from RSV G protein

<400> SEQUENCE: 13

Ile Cys Lys Arg Ile Pro
 1               5

<210> SEQ ID NO 14
<211> LENGTH: 6
<212> TYPE: PRT
<213> ORGANISM: Artificial sequence
<220> FEATURE:
<223> OTHER INFORMATION: Description of artificial sequence: Peptide
      derived from RSV G protein

<400> SEQUENCE: 14
```

```
Ile Cys Ser Asn Asn Pro
  1               5

<210> SEQ ID NO 15
<211> LENGTH: 6
<212> TYPE: PRT
<213> ORGANISM: Artificial sequence
<220> FEATURE:
<223> OTHER INFORMATION: Description of artificial sequence: Peptide
      derived from RSV G protein

<400> SEQUENCE: 15

Ile Cys Lys Arg Ile Pro
  1               5

<210> SEQ ID NO 16
<211> LENGTH: 7
<212> TYPE: PRT
<213> ORGANISM: Artificial sequence
<220> FEATURE:
<223> OTHER INFORMATION: Description of artificial sequence: Peptide
      derived from RSV G protein

<400> SEQUENCE: 16

Ile Cys Ser Asn Asn Pro Thr
  1               5

<210> SEQ ID NO 17
<211> LENGTH: 6
<212> TYPE: PRT
<213> ORGANISM: Artificial sequence
<220> FEATURE:
<223> OTHER INFORMATION: Description of artificial sequence: Peptide
      derived from RSV G protein

<400> SEQUENCE: 17

Ile Cys Lys Arg Ile Pro
  1               5

<210> SEQ ID NO 18
<211> LENGTH: 5
<212> TYPE: PRT
<213> ORGANISM: Artificial sequence
<220> FEATURE:
<223> OTHER INFORMATION: Description of artificial sequence: Peptide
      derived from RSV G protein

<400> SEQUENCE: 18

Phe Val Pro Cys Ser
  1               5

<210> SEQ ID NO 19
<211> LENGTH: 6
<212> TYPE: PRT
<213> ORGANISM: Artificial sequence
<220> FEATURE:
<223> OTHER INFORMATION: Description of artificial sequence: Peptide
      derived from RSV G protein

<400> SEQUENCE: 19

Ile Cys Lys Arg Ile Pro
  1               5

<210> SEQ ID NO 20
<211> LENGTH: 9
<212> TYPE: PRT
<213> ORGANISM: Artificial sequence
<220> FEATURE:
```

<223> OTHER INFORMATION: Description of artificial sequence: Peptide
      derived from RSV G protein

<400> SEQUENCE: 20

Ile Cys Ser Asn Asn Pro Thr Cys Trp
 1               5

<210> SEQ ID NO 21
<211> LENGTH: 10
<212> TYPE: PRT
<213> ORGANISM: Artificial sequence
<220> FEATURE:
<223> OTHER INFORMATION: Description of artificial sequence: Peptide
      derived from RSV G protein

<400> SEQUENCE: 21

Ile Cys Ser Asn Asn Pro Thr Cys Trp Ala
 1               5                   10

<210> SEQ ID NO 22
<211> LENGTH: 6
<212> TYPE: PRT
<213> ORGANISM: Artificial sequence
<220> FEATURE:
<223> OTHER INFORMATION: Description of artificial sequence: Peptide
      derived from RSV G protein

<400> SEQUENCE: 22

Phe Val Pro Cys Ser Ile
 1               5

<210> SEQ ID NO 23
<211> LENGTH: 9
<212> TYPE: PRT
<213> ORGANISM: Artificial sequence
<220> FEATURE:
<223> OTHER INFORMATION: Description of artificial sequence: Peptide
      derived from RSV G protein

<400> SEQUENCE: 23

Ile Cys Lys Arg Ile Pro Ser Lys Pro
 1               5

<210> SEQ ID NO 24
<211> LENGTH: 5
<212> TYPE: PRT
<213> ORGANISM: Artificial sequence
<220> FEATURE:
<223> OTHER INFORMATION: Description of artificial sequence: Peptide
      derived from RSV G protein

<400> SEQUENCE: 24

Phe Val Pro Cys Ser
 1               5

<210> SEQ ID NO 25
<211> LENGTH: 9
<212> TYPE: PRT
<213> ORGANISM: Artificial sequence
<220> FEATURE:
<223> OTHER INFORMATION: Description of artificial sequence: Peptide
      derived from RSV G protein

<400> SEQUENCE: 25

Ile Cys Ser Asn Asn Pro Thr Cys Trp
 1               5

```
-continued

<210> SEQ ID NO 26
<211> LENGTH: 25
<212> TYPE: PRT
<213> ORGANISM: Artificial sequence
<220> FEATURE:
<223> OTHER INFORMATION: Description of artificial sequence: Peptide
      derived from RSV G protein

<400> SEQUENCE: 26

Phe Val Pro Cys Ser Ile Cys Ser Asn Asn Pro Thr Cys Trp Ala Ile
 1               5                  10                  15

Cys Lys Arg Ile Pro Ser Lys Pro Thr
            20                  25
```